(12) United States Patent
Eckert

(10) Patent No.: US 6,603,544 B1
(45) Date of Patent: Aug. 5, 2003

(54) SAMPLE CELL

(75) Inventor: James C. Eckert, Lake Forest, CA (US)

(73) Assignee: Tech Ref, Inc., Anaheim, CA (US)

( * ) Notice: Subject to any disclaimer, the term of this patent is extended or adjusted under 35 U.S.C. 154(b) by 0 days.

(21) Appl. No.: 10/072,710

(22) Filed: Feb. 6, 2002

(51) Int. Cl.[7] ................................................ G01N 1/10
(52) U.S. Cl. ........................ 356/246; 356/244; 356/440
(58) Field of Search ................................ 356/244–246, 356/440; 378/45–47; 422/102, 104

(56) References Cited

U.S. PATENT DOCUMENTS

| | | |
|---|---|---|
| 3,627,432 A | 12/1971 | Bergmann |
| 4,037,109 A | 7/1977 | Hosokawa et al. |
| 4,043,678 A | 8/1977 | Farrell et al. |
| 4,083,638 A | 4/1978 | Sandrock et al. |
| 4,115,689 A | 9/1978 | Won |
| 4,227,810 A | 10/1980 | Sandrock et al. |
| 4,346,299 A | 8/1982 | Mitteldorf et al. |
| 4,409,854 A | 10/1983 | Solazzi |
| 4,448,311 A | 5/1984 | Houser |
| 4,560,269 A | 12/1985 | Baldxzun et al. |
| 4,575,869 A | 3/1986 | Torrisi et al. |
| 4,587,666 A | 5/1986 | Torrisi et al. |
| 4,643,033 A | 2/1987 | Solazzi |
| 4,665,759 A | 5/1987 | Solazzi |
| 4,698,210 A | 10/1987 | Solazzi |
| 4,974,244 A | 11/1990 | Torrisi et al. |
| 5,253,280 A | 10/1993 | Mizuta |
| 5,323,441 A | 6/1994 | Torrisi et al. |
| 5,437,841 A | 8/1995 | Balmer |
| 6,249,345 B1 | 6/2001 | Kraack et al. |

*Primary Examiner*—James Phan
(74) *Attorney, Agent, or Firm*—Fulwider Patton Lee & Utecht, LLP

(57) ABSTRACT

A sample cell for use in X-ray fluorescence devices employs a ring and cup combination to support a radiation-permeable membrane through which a sample is analyzed. The ring component has a protruding lip that is configured to enable the cell to more readily drop into a receiving groove formed about the analyzer aperture.

8 Claims, 2 Drawing Sheets

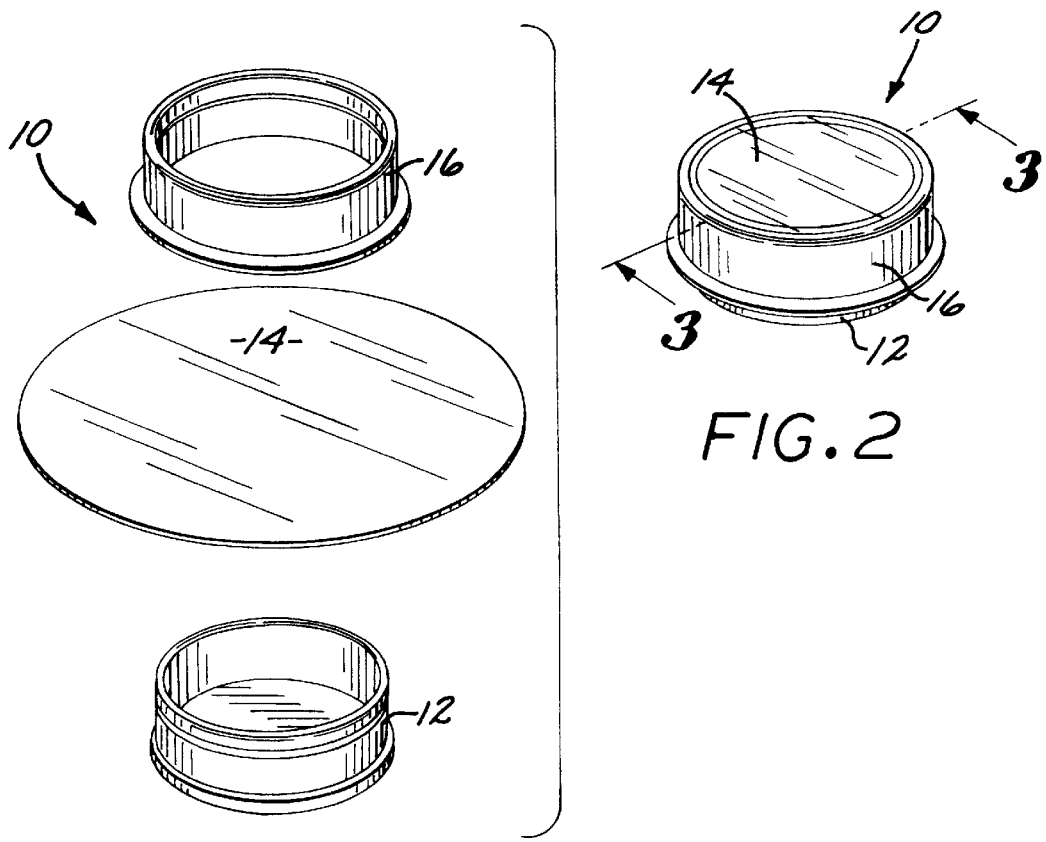
FIG. 1
FIG. 2
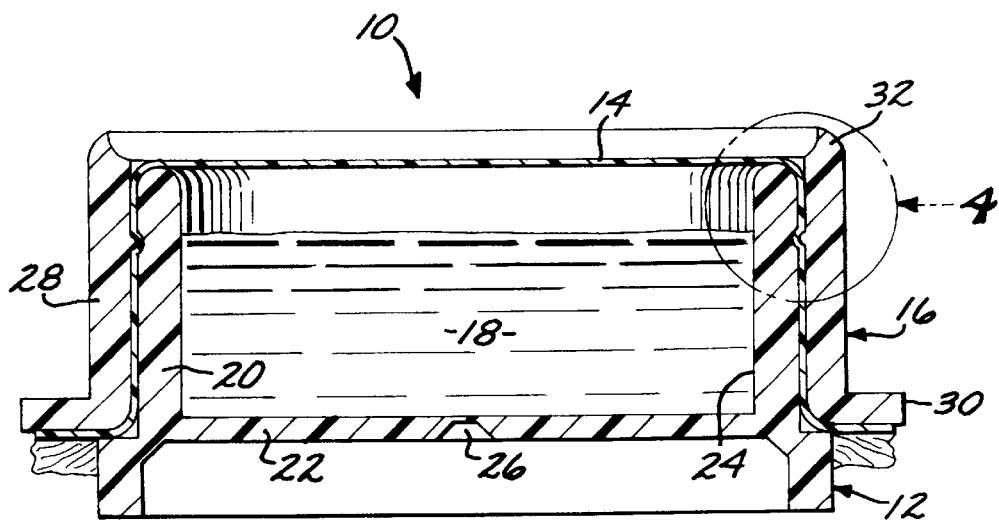
FIG. 3

SAMPLE CELL

BACKGROUND OF THE INVENTION

The present invention relates to an improved sample cell for use with X-ray fluorescence analytical devices.

Sample cells that are used for positioning a sample within an X-ray fluorescence analyzer typically employ a telescopically interfitting cup and ring combination for capturing there between and thereby supporting a radiation-permeable membrane through which the sample is analyzed. After a sample is placed in the cup and the radiation-permeable membrane is positioned across the mouth of the cup, the ring is forced down over the membrane and down along the exterior surface of the cup. The interfitting components serve to capture the membrane there between and pull it taut across the mouth of the cup. Upon inversion of the cup, the sample becomes supported on the flat, wrinkle-free membrane surface on which it is positioned over the X-ray source for analysis. Such sample cells are intended for a single use and are disposed of after the analysis is completed. The cup and ring components are therefore typically molded from a synthetic plastic such as nylon, polyethylene, polypropylene or polyester.

In order to cause the membrane to be tightly and uniformly stretched across the mouth of the cup and to then be maintained in such condition, it had been found to be necessary for the cup and the ring to be very tightly interfitting. The use of such tight tolerances were, however, found to be problematic in that the membrane was thereby prone to bind over the lip of the cup and to then tear or pucker as the ring was pushed into place. While the application of a lubricant reduced the risk of damaging the membrane, considerable time and effort were required in order to properly apply the lubricant so as to avoid contact with the interior of the cup and to thereby avoid contaminating the sample.

Sample cell configurations were subsequently developed to address these shortcomings and included the incorporation of a locking rib and recess combination. A circumferential rib formed on the interior surface of the ring was positioned and dimensioned to cooperate with a circumferential recess formed on the exterior surface of the cup. The inherent flexibility of the plastic used in the construction of the two components allowed the rib to snap into place within the recess as the ring was pushed into place about the cup. This not only served to lock the ring into position on the cup but to also positively hold the membrane there between. A lubricant was additionally incorporated in the plastic to reduce the coefficient of friction between the cooperating components. It was found that the use of silicone oil in combination with virgin polyethylene provided the desired result without the risk of contaminating the sample. The use of the locking mechanism as well as lubricant-containing plastics ensured that a taut and wrinkle-free surface could easily and consistently be achieved and maintained without damaging the membrane during the assembly process. Such device is described in U.S. Pat. No. 4,448,311 which is incorporated herein by reference.

The development of more sensitive X-ray fluorescence analyzing equipment has necessitated the reconfiguration of sample cells. Previously used sample cells had been configured such that the surface of the membrane is positioned outwardly beyond the edge of the fully seated ring component. As a result, the placement of the cell onto a surface while in its inverted state would necessarily cause the membrane to contact such surface and risk the transfer of contamination therefrom. The presence of even minute traces of contamination on the exterior surface of the membrane could compromise the analytical results with the use of the more sensitive analyzing equipment. While the risk of contamination could conceivably be avoided if the sample cell were to be inverted only for final placement over the X-ray source, certain automated analyzers require the cell to first be placed onto a receiving surface while in its inverted state from which it is then automatically transferred to the testing site. The risk of contamination can thereby not readily be avoided.

In order to address this problem, analyzers have been developed that require the membrane of the sample cell to be spaced up off of a flat supporting surface. The spacing of the membrane up off of such a supporting surface has typically been achieved with an increase in the ring height such that its edge extends beyond the edge of the cup and hence the membrane surface when in its fully seated position. In order to allow the membrane to then come into contact with the aperture surface of the analyzer device so as to eliminate any air gap therebetween, the aperture of the device has formed thereabout a receiving groove which is dimensioned to accommodate the protruding edge of the inverted sample cell. Once a selected cell is brought into position above the analyzer's aperture by, for example, an automated sample handling device, it is lowered into place in an effort to allow the protruding lip to drop into the recessed groove. It has however been found that even a very slight misalignment of the cell vis-a-vis the groove can cause difficulties. Should one side of the cell's edge hang up along one edge of the groove while the opposite side drops into the groove, the skewed orientation of the cell will fail to eliminate the air gap between the cell membrane and the aperture surface while the bottom surface of the sample will be angled relative to the X-ray source and sensor. A slightly greater misalignment of the cell vis-a-vis the analyzer aperture could cause the sample cell to remain balanced on the edge of the receiving groove and although such orientation would maintain the bottom of the sample properly angled relative to the X-ray source and sensor, an undesirable air gap will nonetheless remain between the sample cell membrane and the aperture surface. In either scenario, operator intervention would be required in order to rectify the misalignment.

An improved sample cell configuration is therefore needed which can more readily accommodate a slight misalignment of the position of the sample cell vis-a-vis the receiving groove of the analyzer device. The configuration of the sample cell should facilitate its complete receipt in the groove despite small radial or angular misalignments and preclude the assumption of orientations that would require operator intervention.

SUMMARY OF THE INVENTION

The present invention provides a sample cell having a configuration that will more readily drop into the receiving groove that is formed about an analyzer aperture despite slight misalignment of the sample cell relative to the receiving groove. Thus, such sample cell will be less inclined to assume a skewed or an inappropriately offset orientation when deposited onto the aperture surface by an automated sample cell handler such as a turntable or carousel device.

More particularly, the sample cell of the present invention employs a ring element that has a uniquely configured protruding lip on its distal end. The protruding nature of the lip allows the sample cell to be supported on a flat surface so as to automatically maintain the membrane out of contact with such surface and thereby preclude the transfer of contamination therefrom. Additionally, it has been found that the spacing of the membrane up off of a supporting surface serves to reduce the risk of damage to the membrane such as could be caused by a sharp edge or burr that may be present on such surface. The lip is radiused in a manner that has been found to enable the protruding portion of the sample cell to more readily drop into place within the receiving groove that is formed about the aperture surface of the analyzer device. When viewed in cross section, both the exterior edge of the lip as well as the interior edge of the lip are radiused. Moreover, the radius on the exterior edge is formed so as to define a convex surface while the radius on the interior edge is formed with a reverse radius so as to define a concave surface. The smooth exterior surface of the ring along with the incorporation of a lubricant in the material from which the ring is formed further enhances the ability of the sample cell to drop into the analyzer's receiving groove.

The ring element of the sample cell of the present invention additionally has a radially extending flange extending from its proximal end. Such flange enables an automated sample handler such as a turntable or carousel device to pick up the device and move it to and from the analyzer aperture.

These and other features and advantages of the present invention will become apparent from the following detailed description of the preferred embodiment which, taken in conjunction with the accompanying drawings, illustrate by way of example the principles of the invention.

BRIEF DESCRIPTION OF THE DRAWINGS

FIG. 1 is a vertically exploded perspective view of the sample cell of the present invention;

FIG. 2 is a perspective view showing the components of FIG. 1 in their fully assembled state;

FIG. 3 is an enlarged sectional view taken along line 3—3 of FIG. 2;

DETAILED DESCRIPTION OF A PREFERRED EMBODIMENT

Figure 4:
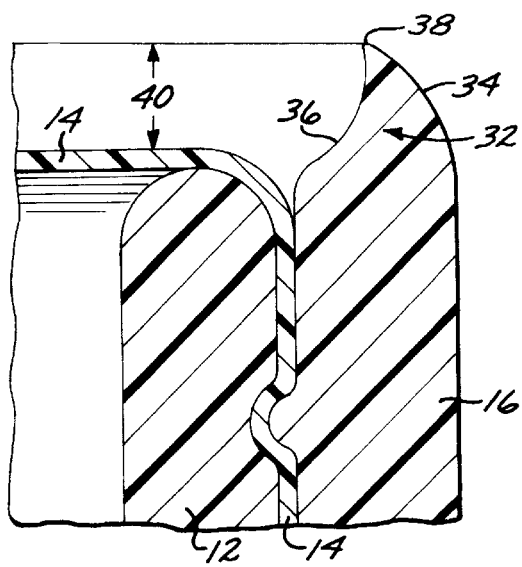
FIG. 4 is a further enlarged view of the encircled area designated 4 in FIG. 3.

The drawings illustrate a preferred embodiment of the sample cell of the present invention. The sample cell is specially configured to (a) space the cell membrane off of a flat supporting surface, (b) allow the cell membrane to directly engage the aperture surface of an analyzer device during the actual analysis step and (c) more readily allow the sample cell to be properly positioned with respect to the analyzer aperture. The latter capability facilitates the automated handling of the sample cell and reduces the need for operator intervention.

Referring now to the drawings, FIG. 1 is an exploded view of the components of the sample cell 10 prior to assembly. The cell includes a cup component 12 and a ring component 16 which, upon assembly, cooperate to support a radiation-permeable membrane 14 across the mouth of the cup. After introduction of a sample into the cup, the membrane is positioned over the mouth of the cup and the ring is pushed down over the membrane into telescoping engagement with the cup. This serves to pull the membrane taut across the mouth of the cup to provide the assembly shown in FIG. 2. For analysis, the cell is inverted and placed over the analyzer aperture so as to be exposed to the X-ray source located within the fluorescence analyzer.

FIG. 3 is an enlarged cross-sectional view of the assembled sample cell 10 shown in FIG. 2. The cup component 12 is of integral molded construction and includes a circular sidewall 20 as well as bottom wall 22 so as to define a cavity 24 for receiving sample 18 therein. A puncturable dimple 26 is formed in the bottom wall to allow the sample cell to readily be vented while in its inverted state. The ring component 16 is also of integral molded construction and includes a circular sidewall 28 that is dimensioned to fit about the exterior of the cup's sidewall. The proximal end of the ring includes a radially extending flange 30 that extends about the cup's entire circumference. The distal end of the ring terminates in a specially shaped lip 32 that extends beyond the surface defined by the membrane 14 that is stretched across the mouth of the cup component 12.

FIG. 4 is greatly enlarged view illustrating the configuration of the distal lip 32 of ring 16. The lip has a specific combination of radii 34, 36 formed therein that has been found to be especially effective in causing the cell to properly drop into a groove that is formed about the periphery of the analyzer device. The radius 34 formed on the exterior of the ring serves to define a convex surface while the reverse radius 36 formed on the interior of the ring serves to define a concave surface. The distal periphery 38 of the lip is spaced beyond the surface defined by the membrane 14 by a predetermined distance 40.

Figures 5, 6:
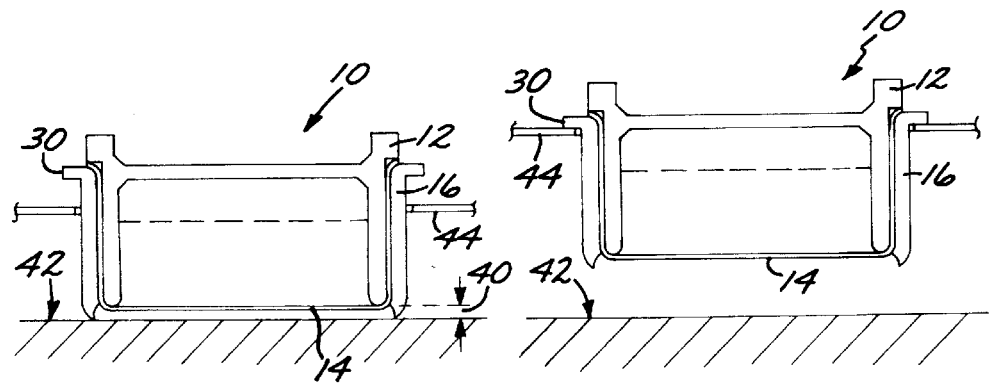
FIG. 5 is cross-sectional view of the sample cell of the present invention in its inverted state while in the 'staged mode'.
FIG. 6 is a cross-sectional view of the sample cell of the present invention in its inverted state while in the 'rotation mode'.

FIG. 5 illustrates the sample cell 10 of the present invention in its 'staged mode' wherein the device is inverted such that the mouth of the cup component 12 is facing downwardly and wherein the device is supported on a flat surface 42. The predetermined distance 40 between the distal periphery 38 of the distal lip 32 and surface defined by the membrane 14 serves to maintain the membrane out of contact with the support surface and thereby precludes the transfer of contaminants therefrom. Additionally, the spaced relationship protects the membrane from damage that may otherwise be inflicted by a sharp surface or burr that may be present on the support surface. In the 'staged mode', the support surface 44 of a sample handling device is lowered out of contact with the radially extending flange 30 of the ring component 16 to allow the sample cell to be supported by a surface therebelow.

FIG. 6 illustrates the sample cell 10 in its 'rotation mode'. The support surface 44 of the sample handler is raised so as to engage the radially extending flange 30 of the ring component 16 and lift the sample cell above the support surface 42. Once clear of the support surface, the sample handling device can then freely move the sample cell, including into a position over the analyzer aperture 46. A sampler handler may consist of a turntable or carousel device wherein a plurality of sample cells are arranged in a circle and the device is rotatable so as to avail an individual sample to analysis. The lowering of the common support surface 44 causes the selected cell to lowered onto the analyzer aperture while all other sample cells are lowered onto support surface 42.

Figures 7, 8:
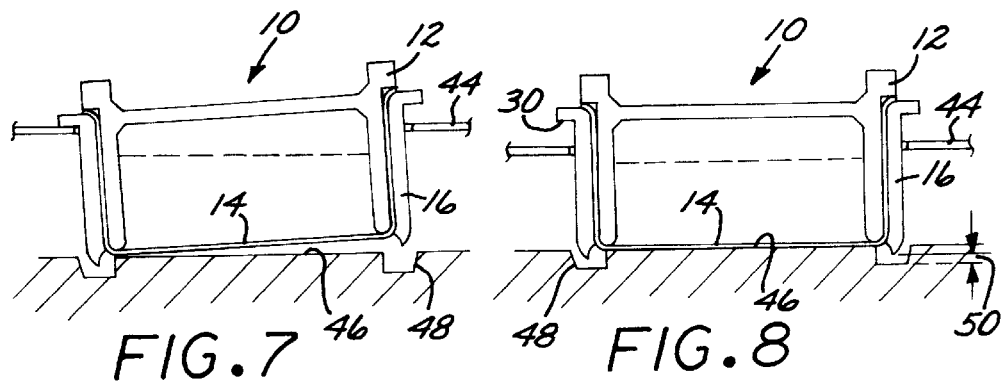
FIG. 7 is a cross-sectional view of the sample cell of the present invention in its inverted state prior to becoming fully seated in the 'analyzing mode'.
FIG. 8 is a cross-sectional view of the sample cell of the present invention in its inverted state while fully seated in the 'analyzing mode.'

FIG. 7 illustrates the sample cell in the process of being lowered onto the analyzer aperture 46. The analyzer aperture is surrounded by a groove 48 that is dimensioned to accommodate the distal lip 32 of the ring component 16 of the sample cell 10. A slight misalignment of the sample cell with respect to the aperture groove may cause either exterior surface 34 of the distal tip 32 or the interior surface 36 of the distal tip, or both, to contact the edge of the groove. Such contact will initially cause the sample cell to become skewed as is shown in the illustration. However, the specific combination of radiused surfaces, i.e., the combination of the convex exterior surface and the concave interior surfaces have been found to be especially effective to shift the cell into a more aligned position and thereby allow the distal lip to become fully received in the groove such that the membrane 14 comes into full contact with the aperture surface.

FIG. 8 illustrates the sample cell 10 of the present invention in its fully seated position over the analyzer aperture surface 46. The support surface 44 of the sample handler has been lowered so as to completely disengage the radially extending flange 30 and the entire membrane 14 surface is in full contact with the aperture surface so as to eliminate any air gap there between. The protrusion of the distal lip 32 of the ring component 16 beyond the membrane 14 is selected such that a gap 50 is maintained between the distal periphery of the lip and the bottom of the groove 48 to thereby ensure that the membrane is able to make full contact with the aperture surface.

Both the cup component 12 and ring component 16 are molded from a synthetic plastic mixed with a lubricant so as to reduce the coefficient of friction between these members and the membrane so as not to break nor pucker nor wrinkle the membrane when it is stretched over the mouth of the cup as the ring is pushed down over the cup. It has been found that where the ring and cup components are molded of a virgin polyethylene, a lubricant such as silicone oil having viscosity of about 60,000 cst in a proportion of approximately 1–5%, preferably 1–2% by weight of silicone oil to virgin polyethylene provides excellent results not only with regard to the interaction of the components with the membrane but also with regard to the interaction of the distal lip with the receiving groove of the analyzer device. It has also been found that with this arrangement the silicone tends to migrate to the surface of the cup and ring members to provide the desired coefficient of friction, yet the silicone will not contaminate the liquid sample 18. The smooth exterior surface of the ring component further enhances the ability of sample cell to drop into the receiving groove.

It must be kept in mind that the sample cell of the present invention as described above is simply illustrative and should be taken by way of an example, and does not in any manner limit the scope and spirit of the invention as claimed. Alterations and modifications may be made by one with ordinary skill in the art, once provided with the teachings of the present invention, which modifications and alterations do not depart from the spirit and scope of the claimed invention. By way of example, any of various locking mechanisms can be employed including a purely interference fit. Accordingly, it is intended that the invention not be limited except by the appended claims.

What is claimed is:

1. A sample cell for supporting a sample on an analyzer aperture surface wherein such analyzer surface has a circular groove formed about its periphery, comprising:
   a circular distal edge formed on the distal end of said sample cell, dimensioned to be received in said groove wherein said distal edge has a radius formed on its exterior side and a reverse radius formed on its interior side.

2. The sample cell of claim 1, wherein said distal edge is formed in a ring component of said sample cell, wherein said ring component is configured so as to be telescopingly received over a cup component of said sample cell and wherein said distal edge protrudes a predetermined distance beyond said cup component upon said ring component being fully received over said cup component.

3. The sample cell of claim 2, further comprising a radiation permeable membrane extending across said cup component, said membrane being held in place by said ring component bearing against said cup component.

4. The sample cell of claim 3, wherein said ring component further includes a radially extending flange near its proximal end to facilitate handling by a sample handling device.

5. The sample of claim 1, wherein said sample cell is molded of plastic and wherein a lubricant is incorporated in said plastic.

6. A sample cell for supporting a sample contained therein flat against an aperture surface of an analyzer device wherein such aperture surface is surrounded by a receiving groove, comprising:
   a cup component having a receiving cavity formed therein and terminating in a mouth;
   a radiation permeable membrane disposed across said mouth;
   a ring component dimensioned for telescopic extension over the exterior of said cup component so as to capture said membrane between the exterior surface of said cup component and the interior surface of said ring component, wherein said ring component terminates in a distal lip and wherein said ring component is further dimensioned such that said distal lip protrudes beyond the distal edge of said cup component when said ring component is fully seated about said cup component, said lip being formed so as to define a convex surface on one side and a concave surface on the opposite side.

7. The sample cell of claim 6, wherein said convex surface is formed on the exterior side of said lip and said concave surface is formed on the interior side of said lip.

8. The sample cell of claim 6, wherein said ring component is molded of plastic and wherein a lubricant is incorporated in said plastic.

* * * * *